US008512950B2

(12) United States Patent
Zassenhaus

(10) Patent No.: US 8,512,950 B2
(45) Date of Patent: Aug. 20, 2013

(54) BIOLAYER INTERFEROMETRY MEASUREMENT OF BIOLOGICAL TARGETS

(75) Inventor: Hans Peter Zassenhaus, Chesterfield, MO (US)

(73) Assignee: Saint Louis University, St. Louis, MO (US)

( * ) Notice: Subject to any disclaimer, the term of this patent is extended or adjusted under 35 U.S.C. 154(b) by 48 days.

(21) Appl. No.: 13/187,190

(22) Filed: Jul. 20, 2011

(65) Prior Publication Data

US 2012/0021416 A1    Jan. 26, 2012

Related U.S. Application Data

(60) Provisional application No. 61/366,384, filed on Jul. 21, 2010.

(51) Int. Cl.
| | | |
|---|---|---|
| C12Q 1/00 | (2006.01) | |
| C12Q 1/68 | (2006.01) | |
| G01N 33/53 | (2006.01) | |
| G01N 33/00 | (2006.01) | |
| G01N 21/00 | (2006.01) | |
| G01N 21/75 | (2006.01) | |
| G01N 33/48 | (2006.01) | |

(52) U.S. Cl.
USPC .................. 435/6.1; 435/4; 435/7.1; 436/86; 436/164; 702/19

(58) Field of Classification Search
USPC ............... 436/86, 164; 435/6.1, 7.1; 702/19
See application file for complete search history.

(56) References Cited

U.S. PATENT DOCUMENTS

| | | | |
|---|---|---|---|
| 7,394,547 | B2 | 7/2008 | Tan |
| 7,445,887 | B2 | 11/2008 | Zuk et al. |
| 7,522,282 | B2 | 4/2009 | Nolte et al. |
| 2004/0096991 | A1 | 5/2004 | Zhang |
| 2005/0254062 | A1 | 11/2005 | Tan et al. |
| 2006/0078920 | A1 | 4/2006 | Pierce |
| 2006/0154320 | A1 | 7/2006 | Zuk et al. |
| 2008/0129981 | A1 | 6/2008 | Nolte et al. |
| 2009/0022659 | A1 | 1/2009 | Olson et al. |
| 2009/0068694 | A1 | 3/2009 | Zuk et al. |

(Continued)

FOREIGN PATENT DOCUMENTS
WO    WO 02094991 A2 * 11/2002

OTHER PUBLICATIONS

Li. African Journal of Biotechnology vol. 8 (20), pp. 5508-5515, Oct. 19, 2009.*

(Continued)

*Primary Examiner* — Robert T. Crow
*Assistant Examiner* — Joseph G Dauner
(74) *Attorney, Agent, or Firm* — Randolph Bretton; The Law Office of Randolph Bretton

(57) ABSTRACT

Disclosed are methods and compositions for the ultrasensitive detection of oligonucleotides, proteins, protein complexes, biomolecules, and infectious agents using a peroxidase driven deposition of substrates onto interferometry capable biosensors, coupled to the specific recognition of the target molecules. More specifically, methods are disclosed to specifically immobilize biological target molecules onto the surface of interferometry capable biosensors and to associate the target molecules with peroxidase enzymes. Through the peroxidase driven deposition of substrates onto the interferometry capable biosensors there is the ability to achieve ultrasensitive detection and quantification of specific target molecules.

14 Claims, 16 Drawing Sheets

(56) References Cited

U.S. PATENT DOCUMENTS

| | | |
|---|---|---|
| 2009/0130105 A1 | 5/2009 | Glaser et al. |
| 2009/0147264 A1 | 6/2009 | Lotze |
| 2009/0148436 A1 | 6/2009 | La Vallie et al. |
| 2009/0191186 A1 | 7/2009 | Bebbington et al. |
| 2009/0274706 A1 | 11/2009 | Bebbington et al. |
| 2010/0062416 A1 | 3/2010 | Bergwerff et al. |
| 2010/0099203 A1 | 4/2010 | Chang et al. |
| 2010/0119511 A1 | 5/2010 | Wang et al. |

OTHER PUBLICATIONS

Abdiche et al., Determining kinetics and affinities of protein interactions using a parallel real-time label free biosensor, Octet, (2008) Anal Biochem 377:209-217.

Choi, J. et al. Development of a Solid-Phase Colorimetric Assay for the Screening of Transglutarninase Activities. The Seoul Journal of Medicine. Sep. 1992. vol. 33. No. 3: 167-173.

Dalsgaard, et al., (2011) Dityrosine, 3,4-Dihydroxyphenylalanine (DOPA), and Radical Formation from Tyrosine Residues on Milk Proteins with Globular and Flexible Structures as a Result of Riboflavin-Mediated Photo-oxidation. J Agric Food Chem, 59, 7939-7947.

International Search Report and Opinion: PCT/US 11/44735, Dec. 8, 2011.

Minamihata et al., (2011) Site-specfic potein cross-linking by peroxidase-catalyzed actvaton of a tyrosine-containing peptide tag. Bioconjug Chem 22(1): 74-81.

Ostdal et al., (1999) Formation of Long-Lived Radicals on Proteins by Radical Transfer from Heme Enzymes-Ð A Common Process?, Archives of Biochemistry & Biophysics 362:105-112.

Ostdal et al., (2002) Reaction between protein radicals and other biomolecules. Free Radio Biol Med 33(2): 201-9.

Relogio et al., (2002) Optimization of oligonucleotide-based DNA microarrays, Nucleic Acids Res vol. 30, No. 11: e51.

You et al., (2006) Design of LNA probes that improve mismatch discrimination, Nucleic Acids Res vol. 34, No. 8 e60.

\* cited by examiner

BIOLAYER INTERFEROMETRY MEASUREMENT OF BIOLOGICAL TARGETS

CROSS-REFERENCE TO RELATED APPLICATION

This application claims priority to provisional application 61/366,384, filed Jul. 21, 2010, hereby incorporated by reference in its entirety.

GOVERNMENT SUPPORT CLAUSE

This work was supported by the National Institutes of Health Grant Number 10237237. The U.S. Government has certain rights in this invention.

FIELD OF THE INVENTION

The invention relates to novel ultra-sensitive methods for measuring specific biological molecules, including DNA, RNA, and protein, using biolayer interferometry.

BACKGROUND

The analysis of DNA has become vital in modern molecular biology and clinical diagnostics. It is now routine for patients with HIV to have their viral isolates analyzed by DNA sequencing for the presence of mutations that cause drug resistance ("genotyping"). Because the amount of DNA found in biological samples is often below detection by commonly used methods, amplification by polymerase chain reaction (PCR) is utilized to not only increase the amount of DNA but to do so specifically—i.e., targets in a heterogeneous mixture of DNAs are specifically amplified with PCR. Although PCR is highly sensitive, successful application of this procedure to detect single molecules of DNA under ideal conditions requires the use of extensive purification of DNA, use of enzymatic manipulations requiring high levels of expertise, and additional downstream manipulations that can be costly and time-consuming to perform because of technical requirements. Many of these procedures are limited to use as research tools because their application for genetic screening is difficult to implement commercially. The Inventor has discovered a method to detect biological targets including specific DNA targets at ultra-high sensitivity using biolayer interferometry. Because of this high sensitivity, the method circumvents the need for PCR amplification of DNA for many applications related to genetic screening. Whereas conventional biolayer interferometry is capable of detecting ~0.2 pmole of DNA, the Inventor has extended that sensitivity >1 million-fold so that ~0.2 attomole (~100,000) DNA targets are detectable. The method which the Inventor has designated Peroxidase Chain Reaction (PxCR), is able to detect as few as 100 DNA, RNA, and protein targets.

SUMMARY OF THE INVENTION

Disclosed are methods and compositions related to detecting a target molecule including exposing a biosensor to a sample containing the target molecule, the surface of the biosensor comprising a capture probe with specific affinity for the target molecule, allowing the target molecule to bind to the capture probe, allowing a target detection molecule to bind to the target molecule, allowing a peroxidase enzyme to bind to the target detection molecule by biotin-streptavidin or other bridging methodology, allowing the peroxidase enzyme to react in the presence of a substrate, whereby the substrate is deposited on the biosensor, and analyzing the results by biolayer interferometry.

Also disclosed are methods and compositions related to a method of detecting a target molecule comprising: exposing a biosensor to a sample containing the target molecule, the surface of the biosensor comprising a capture probe with specific affinity for the target molecule, allowing the target molecule to bind to the capture probe, allowing a target detection molecule to bind to the target molecule, allowing a peroxidase enzyme to bind to the target detection molecule by biotin-streptavidin or other bridging methodology, amplifying the number of bound peroxidase by allowing the peroxidase enzyme to react with a proteinaceous substrate coupled to biotin, whereby the reaction products deposit on the biosensor, allowing streptavidin-peroxidase to bind to the biotin deposited on the biosensor, repeating the amplification as desired, allowing the peroxidase enzyme to react with a substrate, and analyzing the results by biolayer interferometry.

DETAILED DESCRIPTION

Figure 1:
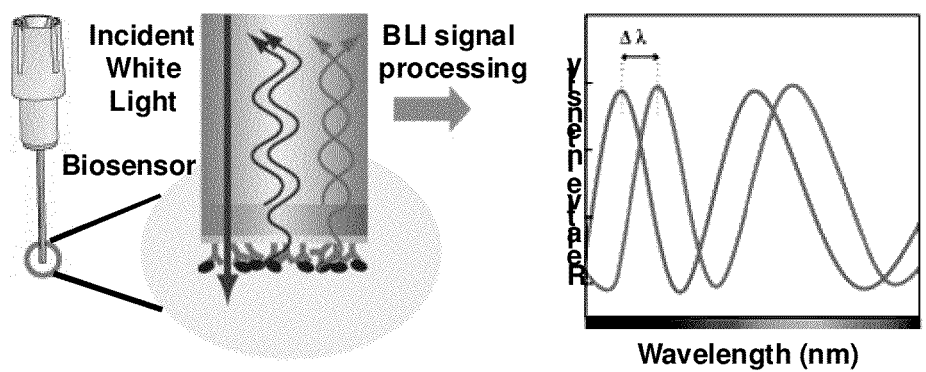
FIG. 1 illustrates the physical principle by which biological targets are detected using biolayer interferometry. White light shines down an optic fiber which terminates at its tip in a thin glass disc from which light reflects both from its internal and external surface. The assembly is hereafter referred to as a biosensor.
Figure 2:
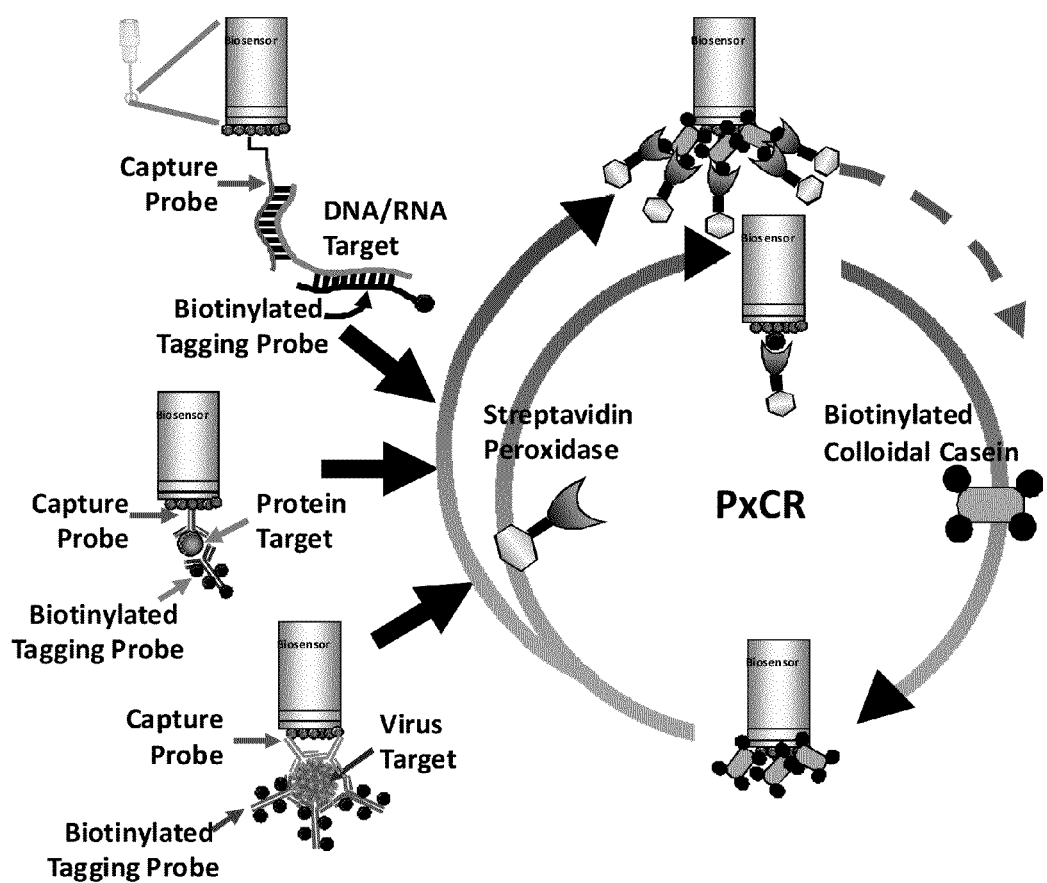
FIG. 2 illustrates a generalized example of Peroxidase Chain Reaction (PxCR) which may include multiple cycles. Targets are captured onto biosensors by specific binding interactions: hybridization for nucleic acids; antibody capture for proteins and infectious particles—e.g., viruses. With the larger infectious particles binding may be cooperative due to their larger size. Bound targets are then tagged with biotin (indicated by solid black dots) by interaction with a second probe which is biotinylated. Signal amplification may proceed in the same manner for all targets. Biosensors are moved into a solution of streptavidin-conjugated horseradish peroxidase (SA-Px) which binds to the biotin-tagged target. The biosensor may then be moved through intervening washes and into a solution of biotinylated colloidal casein, which the Inventor has discovered serves as a preferred substrate for horseradish peroxidase (Px). Enzymatic activity leads to the deposition of biotinylated casein onto biosensors. In the next cycle, the biotinylated casein recruits many more molecules of SA-Px. In real-time PxCR the amount of substrate and enzyme bound to biosensors is reported by biolayer interferometry. With greater sensitivity, the amount of bound SA-Px may be measured by incubation of biosensors in a substrate like diaminobenzidine (DAB), which precipitates onto the biosensor and is measured by biolayer interferometry.

The Inventor has developed technology for the rapid, ultra-sensitive detection of oligonucleotides, proteins, and infectious agents and has designated it Peroxidase Chain Reaction (PxCR). Unlike Polymerase Chain Reaction (PCR), PxCR amplifies signals rather than targets, thereby avoiding the problems associated with contamination of samples, reagents, and work spaces by amplified DNA. Because the signal is amplified, PxCR may detect not only DNA and RNA, but also proteins, protein complexes and infectious particles, including viruses, bacteria, and other microorganisms. PxCR may be used to detect virtually any substance that is able to display an epitope such that it is recognized by an antibody. Peroxidase chain reaction detects the deposition of material on a sensor, hereafter referred to as a biosensor, by interferometry (FIG. 1). The deposition of material reflects amounts of a specific target substance in a test sample. Examples of PxCR are illustrated in FIGS. 2, 3, 4, and 11A. These figures show target molecules, captured onto the biosensor tagged with a biotinylated probe, and then allowed to react, with streptavidin-conjugated peroxidase (SA-Px) via biotin-streptavidin interactions. Amplification takes place by cycling the bound biosensors between solutions, one solution containing a biotinylated substrate for peroxidase and another solution containing additional SA-Px (FIG. 2). Reaction of peroxidase with the substrate causes the substrate to deposit on the surface of the biosensor. The amount of peroxidase (Px) bound to the biosensor is amplified, as the reacted biotinylated substrate deposits on the biosensor, thereby allowing additional binding of SA-Px. Detection occurs either in real-time as biosensors report the amount of deposited enzyme and substrate or, with increased sensitivity, by incubation of the biosensors with a suitable substrate for detecting peroxidase, for example, the staining substrate diaminobenzidine (DAB).

Figure 11A:
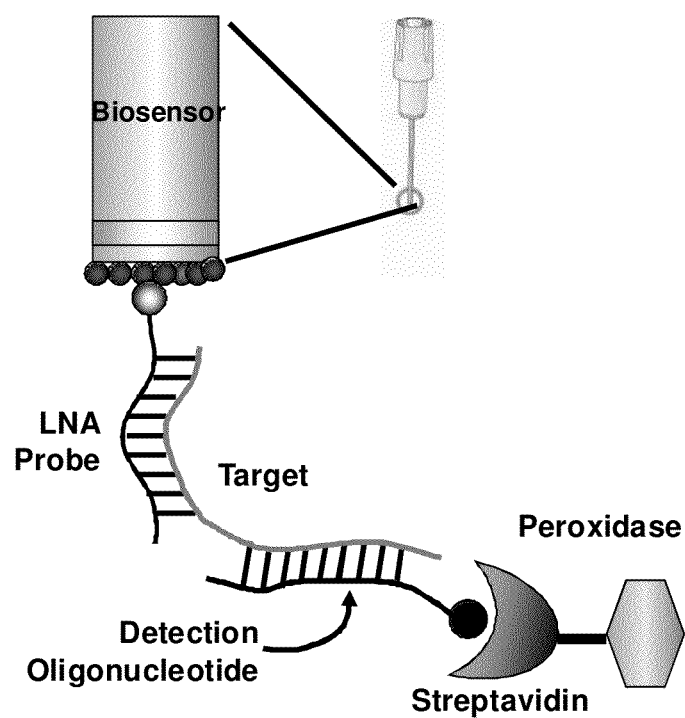
FIG. 11 illustrates the detection of nucleic acid targets. Targets are bound to biosensors by annealing to a capture probe that is covalently crosslinked to the Biosensor. Targets are tagged with biotin (solid black dot) by annealing to a second biotinylated probe. Streptavidin-Peroxidase (SA-Px) is recruited onto biosensors by binding to the biotinylated tagging probe (11A). DNA oligonucleotide targets in the indicated amounts were annealed to biosensors in 20 ul of binding buffer (B: 20 mM Tris pH 7.5, 500 mM NaCl, 1 mM EDTA, 0.1% Tween-20, 100 ug/ml BSA) for 12 hours at room temperature. All subsequent steps were performed robotically in 96-well plates. SA-Px (1 ug/ml) was bound to biosensors in BB+0.5% colloidal casein for 15 min. After further processing and washes, bound peroxidase (Px) activity was measured with a diaminobenzidine-based substrate (ImmPact DAB: Vector Labs). Shown are the enzymatic reaction traces for all 8 biosensors. (B, Left Panel): From those traces the signal was quantified based upon initial enzymatic rates (B, Right Panel).
Figure 11B:
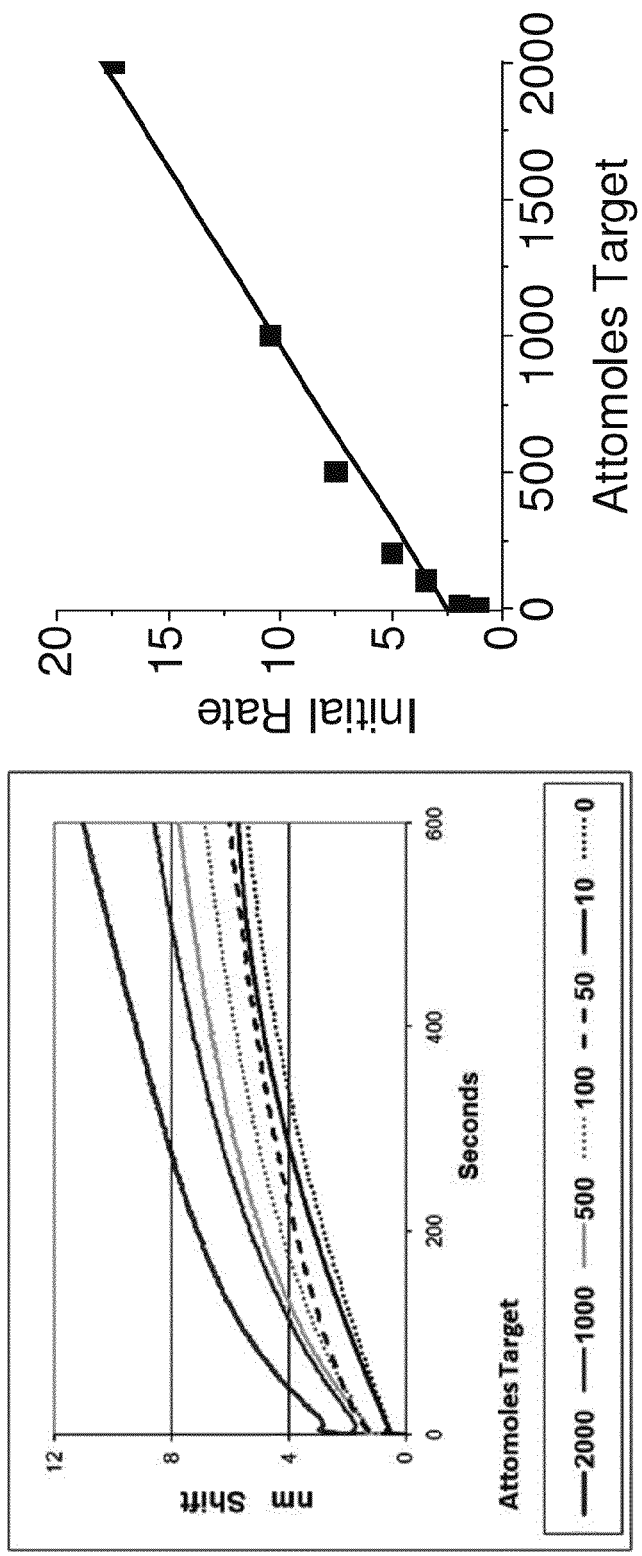

By way of example, and as illustrated in FIGS. 2 and 11A, capture probes may be attached to biosensors through any number of means including covalent attachment and/or chemical crosslinking. In the examples that follow, the Inventor has used Bioconjugate Toolkit reagents from Pierce or carbodiimide (EDAC)/N-hydroxysuccinimide (NHS), as described by ForteBio, the manufacturer of the biosensors used in the examples. Targets may then be attached to the biosensor through specific binding to the capture probe. As illustrated in FIGS. 2 and 11A, the capture of nucleic acid targets is via hybridization to oligonucleotide capture probes. FIG. 2 also illustrates the capture of proteins and infectious particles. For detection of proteins and infectious particles, capture is via binding to antibodies tethered to the biosensor (FIG. 11). The detection of oligosaccharides may also be performed similar to proteins by substituting specific lectins for antibodies to be used as capture probes. Captured targets are then tagged with biotin (solid black dots) by specific binding to a second, biotinylated probe, either another oligonucleotide for detection of nucleic acids or another antibody for detection of proteins and infectious particles (FIG. 2), or in the detection of oligosaccharides, biotinylated lectins. Finally, SA-Px is recruited onto the biosensor through the binding of streptavidin to biotin. Peroxidase activity is detected by incubation of biosensors in a substrate whose reaction product attaches to the biosensor and is reported by nm shift. In the examples that follow, a preferred substrate diaminobenzidine (DAB) was used as described. This method gives detection sensitivities in the femto to attomole range as demonstrated in Example 5 and (FIG. 11B left and right).

Manipulation of the biosensors, reagents, and reaction vessels may be performed robotically. Because the capture of targets by the biosensor relies on the specific recognition of target molecules, including specific hybridization for nucleic acids and specific antibody affinities for proteins and infectious particles, sample preparation may be minimal allowing the use of semi purified or unpurified samples. For RNA targets, preparation may merely be solubilization to release genomic RNA from a virus or host cell. For proteins and infectious particles with exposed epitopes, preparation may be as simple as dilution into the loading solution. Specificity is high similar to PCR since, in a preferred embodiment, detection requires that the targets bind to two separate probes, a capture probe tethered to the biosensor and a biotinylated tagging probe.

The physical principle utilized by the Inventor to detect biological target molecules including DNA, RNA, and proteins, is biolayer interferometry. White light shines down an optic fiber which terminates at its tip in a thin glass disc from which light reflects both from its internal and external surface (FIG. 1). This assembly hereafter is referred to as a biosensor. Reflection from the internal surface constitutes the reference beam while reflection from the external surface constitutes the signal beam. The phase of the reflected signal beam is modulated by the number of biomolecules or reacted substrates that bind to the tip of the biosensor. Thus, the reference and signal reflections show constructive and destructive interference at different wavelengths. This interference pattern is captured by a spectrometer coupled to a photodetector. A change in the number of molecules bound to the tip of the biosensor causes a shift in the interference pattern which is reported as a wavelength shift (nm). The magnitude of the wavelength shift is a direct measure of the number of biomolecules bound to the tip of the biosensor (see Abdiche et al., (2008) Anal Biochem 377:209-217, the contents of which are herein incorporated by reference in their entirety). Also, an example of biolayer interferometry apparatus, including a bio-layer interferometry biosensor, is described in U.S. Pat. No. 7,394,547, the contents of which are herein incorporated by reference in their entirety.

The inventor has discovered that the sensitivity for detection of a specific target molecule is increased from thousands to more than one million fold when peroxidase enzymes are attached to the surface of the biosensor via a target molecule, and the results are analyzed by biolayer interferometry. The reaction products produced by the peroxidase enzyme and an appropriate substrate bind to the surface of the biosensor where they are detected by biolayer interferometry. By attaching peroxidase to the biosensor via a specific target molecule, the number of peroxidase molecules, and therefore the amount of reacted substrate deposited on the surface of the biosensor are directly proportional to the amount of bound target molecule. The substrate may be any substance that is deposited on the biosensor by the action of peroxidase and is detected by interferometry. Substrates include proteins such as colloidal casein and non-protein such as DAB. The Inventor has discovered that biotinylated colloidal casein is a most preferred substrate for peroxidase in PxCR and may be reacted in the absence of hydrogen peroxide. While not wishing to be bound by theory, the Inventor hypothesized that the biochemistry underlying PxCR using a colloidal casein substrate is related to the spontaneous generation of free radicals in the biotinylated colloidal casein substrate. These free radicals rapidly decompose into organic peroxides which support Px activity towards casein so as to generate additional free radicals. This "free radical chain reaction" mechanism may be similar to that proposed for the hydrogen peroxide-independent peroxidation of indole-3-acetic acid (Krylov et al., (1996) J. Phys. Chem. 100:913-920).

The Inventor has also found other proteins to be useful substrates preferably when reacted in the presence of Immobilon chemiluminescent HRP substrate (Millipore) or equivalent solutions. While not wishing to be bound by theory, the Inventor believes that peroxidase catalyzes the decomposition of hydrogen peroxide, generating free radicals as reaction products. These free radicals then go on to react with a substrate causing the substrate to be deposited on the surface of the biosensor. The substrate is preferably a protein, by way of example bovine serum albumin (BSA) or milk proteins (e.g., non-fat dried milk commonly used for blocking of non-specific binding in antibody based assays and available from commercial food stores).

Substrates used in PxCR may be any molecule that is deposited on biosensors by the action of peroxidase. The substrate may also be biotinylated, or possess another form of bridging which may be exploited to recruit peroxidase. By way of example, digoxigenin may be conjugated to a substrate as a bridging molecule which then would recruit peroxidase using covalent anti-digoxigenin antibody conjugated to peroxidase.

Peroxidase substrates and their reaction conditions are well known in the field. It is appreciated that a variety of substrates and reaction conditions may be applied to the instance invention, provided the substrate, once reacted, is ultimately deposited on the surface of the biosensor. Proteinaceous substrates and reaction conditions for peroxidase that may be adapted to PxCR have been described in the art. For example see Ostdal et al., (2002) Free Radic Biol Med 33(2): 201-9 and Minamihata et al., (2011) Bioconjug Chem 22(1): 74-81, hereby incorporated by reference in their entirety.

Deposition of the reacted substrate is registered by the biosensor as biolayer interference. Non-proteinaceous substrates are also effective. A widely used histochemical substrate for peroxidase is diaminobenzidine (DAB). The Inventors have shown that DAB is also deposited on biosensors by the action of peroxidase and that this deposition is also detected as biolayer interference. Because peroxidase undergoes many reaction cycles per minute, a large amount of substrate is deposited on a biosensor for each bound peroxidase enzyme. The direct or indirect linking of peroxidase with specific capture probes provides specific recognition of target molecules. The further utilization of peroxidase substrates that are linked to yet additional peroxidase enzymes provides for increased amplification of the detected signal.

Figure 3:
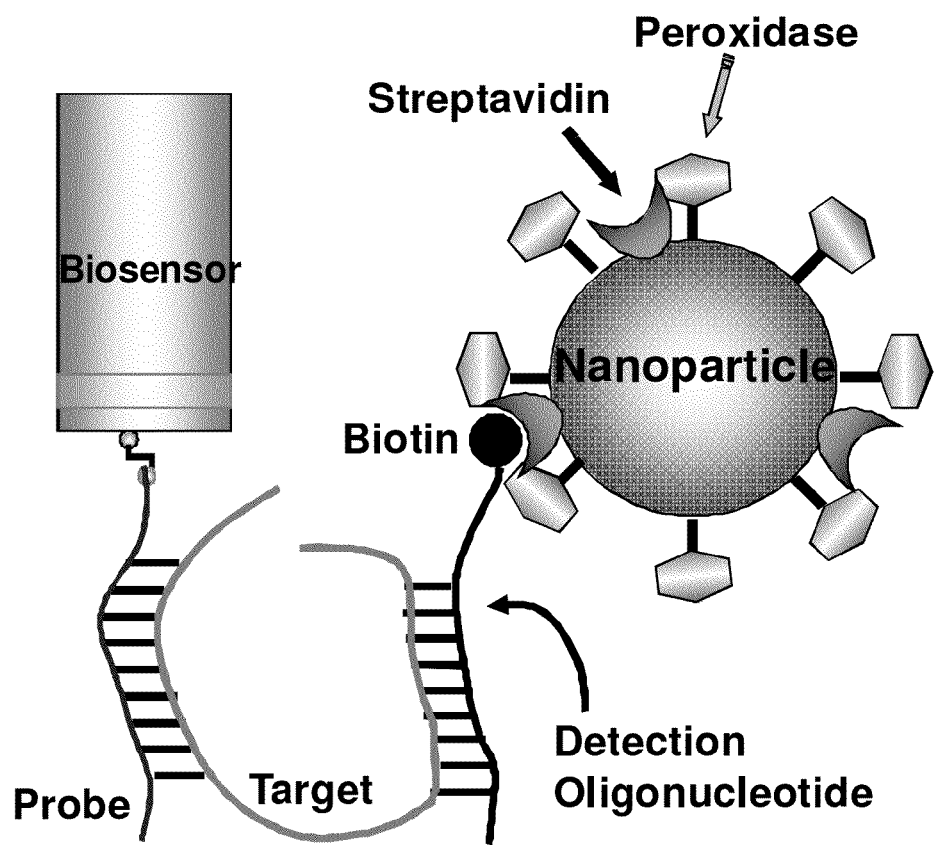
FIG. 3 illustrates one example of the ultrahigh detection sensitivity of DNA targets using nanoparticles. Capture probes (Probes) coupled to biosensors by chemical crosslinking, hybridize to targets which are then tagged with a biotinylated target detection oligonucleotide. Streptavidin coated nanoparticles containing horseradish peroxidase are recruited to the biosensor bound target molecule by biotin on the target detection oligonucleotide.

The attachment of the target molecule to the biosensor may be direct or indirect (FIG. 3). The target molecule may be bound directly to the biosensor or preferably, may be bound via a capture probe with a specific affinity for the target molecule. Examples of capture probes with affinity for a target molecule where the target molecule is a nucleic acid include oligonucleotides which will hybridize to the target, either DNA or RNA. Examples of capture probes with affinity for target molecules where the target molecule is an antigen include antibodies which will specifically bind to the target antigen. Antigens include any substance capable of invoking an immune response in an animal which generates antibodies, including chemical compounds, proteins, lipids, fatty acids, carbohydrates, combinations thereof and chemically modified variations thereof. In addition to oligonucleotides and antibodies, examples of capture probes also include any molecule with a specific affinity for a target molecule, by way of example, lectins, oligosaccharides, enzymes and receptors, which have a specific affinity for substrates, agonists, or antagonists. Direct attachment of capture probes includes chemical crosslinking for example Bioconjugate Toolkit reagents from Pierce or carbodiimide EDAC/N-hydroxysuccinimide (NHS), as described by ForteBio, the manufacturer of these biosensors (also see Staros, J. V., et al (1986) Anal. Biochem 156:220-2). Examples of target molecules include any molecule which may be attached with specificity to the biosensor or capture probe and used directly or indirectly to recruit peroxidase enzymes. Attachment of the target molecule or the capture probe to the biosensor may be via a biotin-streptavidin bridge or other binding methods. By way of example streptavidin may be bound to the surface to the biosensor and the target molecule or capture probe may be coupled to biotin whereby the affinity of biotin for streptavidin provides the means for attachment.

The attachment of peroxidase to the target molecule may be direct or indirect. Peroxidase may be directly coupled to the target nucleic acid or protein, or preferably the attachment of peroxidase is indirect when for example peroxidase is coupled to a target detection molecule selected for its ability to specifically bind to the target molecule. Where the target molecule is a nucleic acid, examples of target detection molecules include oligonucleotides that hybridize or bind to the target nucleic acid. Where the target is an antigen, the target detection molecule includes antibodies that specifically bind to the target antigen. Where the target is an oligosachharides the target detection molecule may be a lectin. In some instances, a capture probe and a target detection molecule may be identical or nearly identical. These target detection molecules are in turn directly or indirectly coupled to a peroxidase enzyme.

Any number of amplification scenarios may be envisioned which allow for additional peroxidase enzymes to be recruited to the biosensor via the target molecule, the target detection molecule, or combinations thereof. By way of example, increased sensitivity may be achieved by linking peroxidase enzymes to target molecules via a biotin-streptavidin bridge. Biotin-streptavidin bridging systems and amplification methods are known in the art associated with antibody based assays. A target detection molecule coupled to biotin specifically binds to the target molecule whereby the biotin in turn due to its affinity for streptavidin is used to bind a streptavidin molecule that is coupled to one or more peroxidase enzymes. The streptavidin-peroxidase may be a complex comprising multiple peroxidase enzymes further increasing the number of peroxidase enzymes recruited to the biosensor. In addition, the streptavidin-peroxidase may contain multiple streptavidin, thereby binding additional biotinylated target detection molecules, thereby binding additional target molecules, and thereby repeating the binding cycle so the number of peroxidase enzymes recruited to the biosensor is greatly increased, but remains dependent on the amount of target molecule being detected. In one example nanoparticles coated with hundreds to thousands of streptavidin molecules are used for binding to biotinylated target detection molecules (FIG. 3). Each nanoparticle is then capable of recruiting multiple peroxidase molecules resulting in the linkage of many peroxidase enzymes to a single target or target detection molecule.

The inventors have discovered that the use of certain substrates coupled to biotin will further increase the sensitivity. As described above, peroxidase activity results in the deposition of certain substrates on the surface of the biosensor, for example: proteins, such as bovine serum albumin (BSA) and milk proteins, when reacted in the presence of Immobilon chemiluminescent HRP substrate (Millipore) or the equivalent. A most preferred substrate is colloidal casein which does not require Immobilon chemiluminescent HRP substrate (Millipore) or hydrogen peroxide. Yet another amplification strategy uses these substrates and a bridging system to further increase sensitivity. A most preferred example of a bridging is biotin-streptavidin methodology. Antibodies and antigens may also be used as bridging systems. By way of example, digoxigenin may be conjugated to a detection molecule or a substrate as a which then would recruit peroxidase using anti-digoxigenin antibody conjugated to peroxidase.

Figure 4:
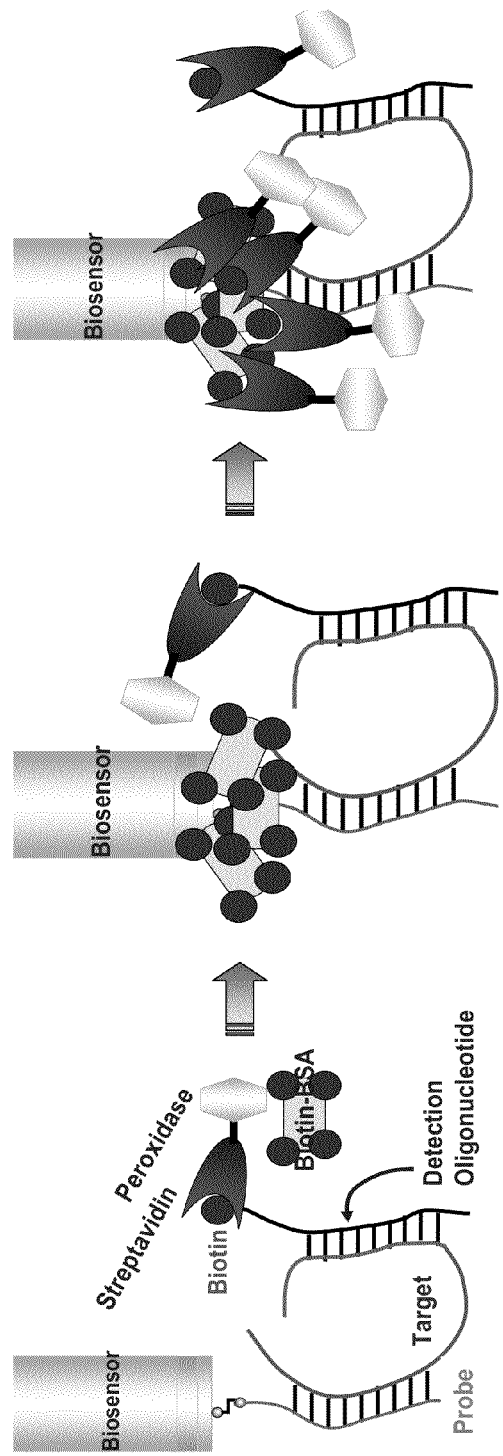
FIG. 4 illustrates the amplification of the number of peroxidase molecules recruited onto a biosensor and the use of a biotinylated protein as a substrate. Peroxidase, bound to the biosensor via target molecules is reacted in a solution containing a biotinylated proteinaceous substrate, by way of example biotin-BSA or biotinylated colloidal casein so that enzymatic activity drives the adsorption or deposition of the biotinylated proteinaceous substrate, onto the biosensor. The presence of biotin on the biosensor is then used to recruit peroxidase to biosensor by the addition of a solution containing streptavidin-peroxidase.

By way of example, the sensitivity of any of the above described assays may be enhanced by providing proteinaceous substrates bonded to biotin such as BSA-biotin or milk protein-biotin, or colloidal casein-biotin, under reaction conditions that result in the deposition of the substrate on the biosensor. In a most preferred example colloidal casein-biotin, supplied as a substrate, in any of the above described assays will result in the colloidal casein-biotin being deposited on the tip of the biosensor (FIG. 4). The biosensor may then be exposed to a streptavidin-peroxidase or streptavidin peroxidase containing nanoparticles thereby recruiting more peroxidase enzymes to the tip of the biosensor and further increasing detection sensitivity. The biosensor may then be reacted with additional colloidal casein-biotin and streptavidin-peroxidase repeating the cycle one or more times to further enhance the number of peroxidase on the surface of the biosensor. In a most preferred example a chemical substrate such as DAB may be used to enhance detection. Peroxidase activity may then be detected as biolayer interferometry. Protein substrates and chemical substrates such as the chemical substrates DAB may be used together or in any combination. Maximum sensitivity (i.e., detection of zeptomole and lower amounts of DNA) is achieved by using any or all of the above amplification strategies so that multiple peroxidase molecules become linked to a single target.

Biotin may be coupled to proteins through any number of methods know in the art including, amine biotinylation, carbohydrate biotinylation, carboxyl biotinylation, sulflhydryl biotinylation, and photoreactive biotinylation. Biotin may be coupled to oligonucleotides through any number of methods, for example terminal deoxynucleotidyl transferase (TdT) to catalyze nontemplate-directed nucleotide incorporation onto the 3'-OH end of single-stranded DNA. Oligonucleotides coupled to biotin may also be purchased commercially. Reagents and methods are available from commercial suppliers including Thermo Fisher Scientific, PO Box 117, Rockford, Ill. 61105 USA.

In one preferred embodiment is a method of detecting a target molecule, by attaching a capture probe to a biosensor, allowing the capture probe to bind to the target molecule from a sample solution, allowing a detection molecule to bind to the target molecule whereby the detection molecule is conjugated with biotin, allowing streptavidin-peroxidase to bind to the biotin, reacting the peroxidase with a substrate that deposits on the biosensor and is detected by interferometry.

In another preferred embodiment is a method of detecting a target molecule, by attaching a capture probe to a biosensor, allowing the capture probe to bind to the target molecule from a sample solution, allowing a detection molecule to bind to the target molecule whereby the detection molecule is conjugated with biotin, allowing streptavidin-peroxidase to bind to the biotin, amplifying the number of peroxidase by reacting the peroxidase with a biotinylated proteinaceous substrate that deposits on the biosensor, allowing additional streptavidin-peroxidase to bind to deposited biotin, repeating the amplification as desired, and reacting the peroxidase with a substrate that deposits on the biosensor and is detected by interferometry.

In a most preferred embodiment is a method of detecting a target molecule, by attaching a capture probe to a biosensor, allowing the capture probe to bind to the target molecule from a sample solution, allowing a detection molecule to bind to the target molecule whereby the detection molecule is conjugated with biotin, allowing streptavidin-peroxidase to bind to the biotin, amplifying the number of peroxidase by reacting the peroxidase with a biotinylated colloidal casein substrate that deposits on the biosensor, allowing additional streptavidin-peroxidase to bind to deposited biotin, repeating the amplification as desired, reacting the peroxidase with DAB, or the equivalent, and detected by biolayer interferometry.

In another preferred embodiment is a method of detecting a target molecule, by attaching a capture probe to a biosensor, allowing the capture probe to bind to the target molecule from a sample solution, allowing a detection molecule to bind to the target molecule whereby the detection molecule is conjugated with biotin, allowing streptavidin-peroxidase to bind to the biotin, amplifying the number of peroxidase by reacting the peroxidase in the presence of Immobilon chemiluminescent reagent or an equivalent solution and a biotinylated bsa substrate that deposits on the biosensor, allowing additional streptavidin-peroxidase to bind to the deposited biotin, repeating the amplification as desired, reacting the peroxidase with DAB, or equivalent, and detected by biolayer interferometry.

Biolayer Interferometry Detection

Macromolecules bind specifically to the tip of the biosensor depending on the nature of functionalities that are covalently attached to the tip. As described above the specific detection of DNA or RNA targets may be achieved by the covalent attachment of complementary oligonucleotides which bind via hybridization only to specific DNA sequences found uniquely in the desired target. The ForteBio OCTET was developed for measuring protein-protein interactions (e.g., antibody-antigen binding). The inventors have demonstrated that it is also capable of detecting DNA targets by hybridization. Using conventional methods, the lower limit for sensitivity of detection is approximately 0.2 pmole of target protein or DNA bound to the biosensor. Increased sensitivity is achieved once peroxidase molecules are recruited to the biosensor, and the detection of peroxidase molecules which are associated with a biological target is performed by biolayer interferometry, for example a ForteBio OCTET as described in U.S. Pat. No. 7,394,547, the contents of which are herein incorporated by reference in their entirety. The OCTET is a bench top instrument that uses biolayer interferometry for real-time detection of macromolecules that bind to a fiberopitic, referred to herein as a biosensor. The biosensor is a rigid, thin optic fiber that is typically incubated in a sample solution contained in a 96-well micro titer plate. Macromolecules that bind to the tip of the biosensor are detected due to the reflectance they cause of light shone down the biosensor. The reflected light interferes with the incident light and that interference is measured by a spectrophotometer built into the instrument (FIG. 1). Reflection from the internal surface constitutes the reference beam while reflection from the external surface constitutes the signal beam. The phase of the reflected signal beam is modulated by the number of biomolecules that bind to the tip of the biosensor. Thus, the reference and signal reflections show constructive and destructive interference at different wavelengths. This interference pattern is captured by a spectrometer coupled to a photodetector. A change in the number of molecules bound to the tip of the biosensor causes a shift in the interference pattern which is reported as a wavelength shift (nm). The magnitude of the wavelength shift is a direct measure of the number of biomolecules bound to the tip of the biosensor (FIG. 1) (see Abdiche et al., (2008) Anal Biochem 377:209-217, the contents of which are herein incorporated by reference in their entirety).

The quantity of bound macromolecules determines the amount of interference which is displayed graphically in real-time using computer peripherals. The biosensor is robotically controlled so that it can be incubated in up to 12 different wells, for varying times in any order as programmed by the user. Eight separate biosensors can be operated at one time which gives the instrument the capability for multiple, simultaneous analyses.

Ultra-Sensitive Interferometry May be Used in Combination with Other Methods of Analysis.

The invention can also be combined with other methods of detection or analysis, for example assays that alter the specificity of detection for the target molecule. Assay conditions, for example temperature may be altered such that the target nucleic acids hybridize to an oligonucleotide capture probe under more stringent or less stringent conditions. This is useful in detecting small variations between genetic sequences in a target nucleic acid. Locked nucleic acid (LNA) technology allows for enormous design flexibility in order to synthesize oligonucleotides that have high mismatch discrimination. Mutant and wild-type DNAs that differ by a single nucleotide can be discriminated by hybridization based upon the difference in the thermal stability (i.e., the ΔTm) of duplexes that are a perfect match versus a single mismatch. But the ΔTm using conventional oligonucleotides is often less than 10° C. and is highly variable depending on the mismatched nucleotide pair and the surrounding DNA sequence (Relogio et al., (2002) Nucleic Acids Res 30:e51, the contents of which are herein incorporated by reference in their entirety). Thus, mutants present in a mixture of wild-type and mutant molecules at less than 10% frequency are not reliably detected. The inventors have devised oligonucleotides synthesized from LNA nucleotides so that mutants are routinely identified at frequencies of 1% and below. LNA's are nucleotide analogs where the nucleotide is "locked" into a C3'-endo conformation. In duplexes between LNA oligonucleotides and canonical DNA, the helix twists to adopt an A-form structure rather than the usual B-form. In the A-form, intrastrand base-stacking interactions contribute more to the stability of the duplex compared to the B-form. Consequently, the Tm of an A-form duplex is higher and the destabilizing effect of a mismatch is greater. For instance, in studies comparing LNA 8-mers to their canonical counterparts, where both were hybridized to normal DNA complements, increases in the Tm of LNA duplexes ranged from 30-40° C. while the ΔTm of a mismatch increased to 20-30° C. compared to the 5-10° C. for mismatches with canonical duplexes. Because the effects of LNA nucleotides on the Tm of LNA:DNA duplexes are additive, the composition of oligonucleotide capture probes can be adjusted to a specified Tm (You et al., (2006) Nucleic Acids Res 34:e60, the contents of which are herein incorporated by reference in their entirety). It is this unprecedented combination of high Tm's and high mismatch ΔTm's with LNA oligonucleotides that leads to better than 100-fold discrimination between mutant and wild-type nucleic acids.

Because $T_m$'s are high, oligonucleotides can be as short as 7-mers. The mismatch position can be anywhere within the oligonucleotide other than at the termini; and the composition (i.e., number of LNA nucleotides) can be varied to fine tune $T_m$'s. Since discrimination of single-base mismatches can vary greatly depending on sequence context and the nucleotide mismatch being interrogated (for example, the G:T mismatch can be difficult to detect), this design flexibility makes it highly likely that well-performing oligonucleotides can be made to interrogate most any site in a target nucleic acid molecule for the presence of a mutation.

As described above, a variety of amplification schemes can be devised to further increase the number of peroxidase molecules bound to each DNA target on a biosensor, resulting in even greater signals. Overall, increases in sensitivity of detection by more than 1-million fold have been achieved so that the binding of ~100,000 DNA molecules (i.e., ~0.2 attomoles) to a biosensor can be detected.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLES

Methods and Materials

Enzymatic Amplification of Signals.

Figure 7:
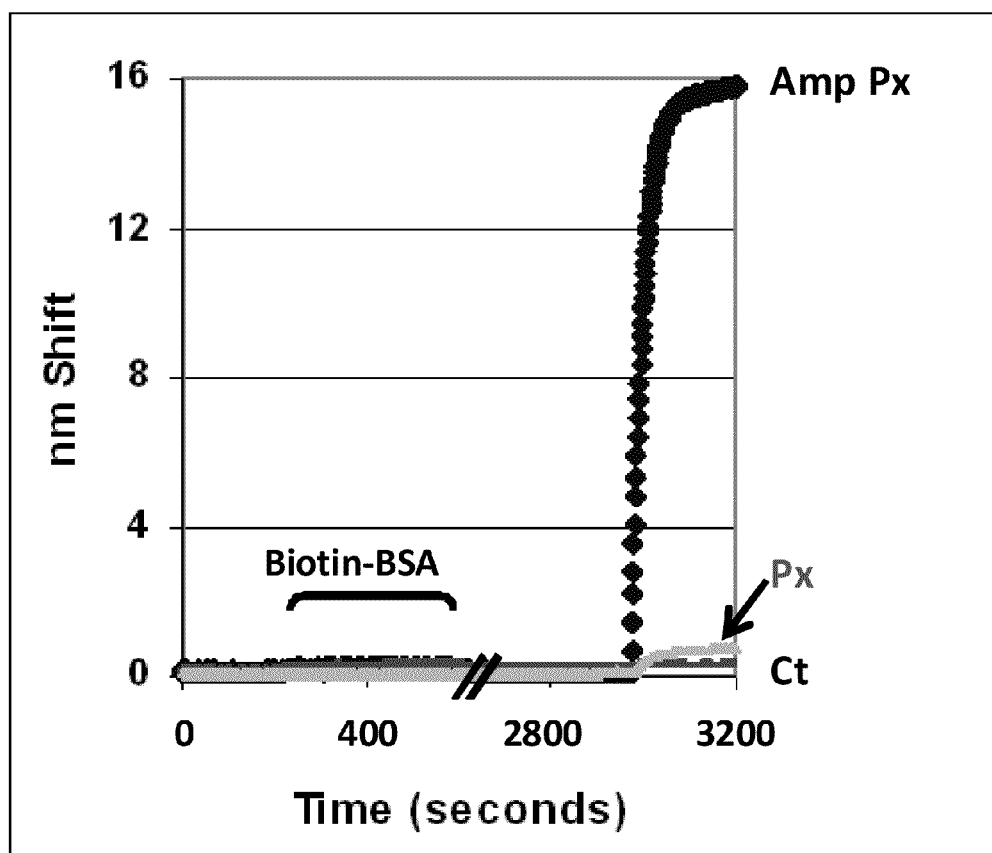
FIG. 7 illustrates amplification of bound peroxidase using a biotinylated protein substrate. Streptavidin biosensors were incubated off-line in 10 pg/ml biotin-peroxidase followed by streptavidin-peroxidase. Bound peroxidase was allowed to react in the presence of a solution of biotin-BSA. A solution of streptavidin-peroxidase was then applied to allow the binding of additional peroxidase enzyme. A subsequent incubation with streptavidin-peroxidase allowed the binding of additional peroxidase enzyme. Total peroxidase bound to the biosensor was then detected in reactions containing diaminobenzidine as substrate.

Detection of bound target DNAs relies on the enzymatic activity of horseradish peroxidase that is recruited onto biosensors. The amount of peroxidase bound to biosensors can be amplified by incubation in biotinylated-BSA, which serves as a substrate for the pre-existing peroxidase that is bound to DNA targets. Peroxidase activity drives binding of biotinylated-BSA to the biosensor, which, in turn, allows for recruitment of many more streptavidin-peroxidase conjugates. As shown in FIG. 7 this strategy amplifies signals at least 20-fold. For ultra-high sensitivity, peroxidase-coated nanoparticles may be employed instead of streptavidin-peroxidase conjugates in the final incubation step so as to recruit larger numbers of peroxidase enzymes onto the biotinylated-BSA that is deposited on biosensor tips.

The nanoparticles used were 0.37 µm polystyrene microspheres containing covalently attached streptavidin. Once bound to biotinylated DNA targets on the biosensor, they were coated with peroxidase by sequential incubations in biotinylated anti-streptavidin (Vector Laboratories) and polymeric streptavidin-peroxidase (Sigma). Polystyrene streptavidin microspheres are available in sizes from 50 nm to 20 µm and similar beads made from silica are available in sizes from 150 nm to 5 µm (Bangs Labs and Spherotech). Although larger streptavidin spheres have greater surface area and therefore bind more biotinylated peroxidase, larger spheres may also suffer from crowding effects on the biosensor. The surface area of a biosensor is ~3×10$^5$ micron$^2$; assuming an even distribution, 10,000 bound DNA targets yields a surface density of 1 DNA molecule per 30 micron$^2$, which calculates to a mean spacing between DNA molecules of ~6 microns. Larger spheres, therefore, have a greater likelihood of crosslinking DNA targets, leading to decreased sensitivity and non-linear responses as the number of bound DNA targets increase. The size and composition (polystyrene versus silica) of microspheres also affect their non-specific adsorption to surfaces, clumpiness, ease of handling (e.g., washing), and suspension characteristics.

Hybridizations were performed for 3 hours at room temperature (RT) with biosensors incubated in 20 µl 3×SSC/0.05% Tween 20 or binding buffer (BB: 20 mM Tris-HCl pH 7.6, 1 mM EDTA, 500 mM NaCl, 0.1% Tween 20, 100 µg/ml BSA), to which denatured salmon sperm DNA is added as carrier at 100 µg/ml. Targets were quantified based upon their OD$_{260}$ and diluted in hybridization buffer to the desired number of targets. Detection oligonucleotides were held constant at 10$^9$/ml. As sensitivities increase and therefore the concentration of DNA targets decreases in reactions, it is expected that hybridization rates will decrease due to mass action. It is also expected that the use of molecular crowding reagents (PEG, dextran sulfate) will enhance hybridization rates. Following hybridization, biosensors were washed in BB and incubated for 30 min in 50 µl BB plus 0.1 µg/ml streptavidin peroxidase (Sigma or ThermoFisher). Non-specific adsorption of streptavidin-peroxidase conjugates to biosensors has been shown to be very low in BB. Background absorption may be further reduced by the use of commercial blockers (SuperBlock, Pierce; SNIPE, Biocare Medical) or by the use of lower concentrations of streptavidin-peroxidase conjugates or complexes.

Amplification using biotin-BSA (Sigma, 8-12 biotins/molecule) was performed with biosensors incubated at RT for 5 min in 200 µl chemiluminescent detection reagent (Millipore) containing 10 µg/ml biotin-BSA plus 200 µg/ml normal BSA (99% fatty acid free, Sigma). Peroxidase driven adsorption of BSA (and other protein substrates, including milk proteins, e.g., non-fat dry milk, and gelatin) onto biosensors occurs at faster rates and to higher levels in the Millipore reagent compared to standard peroxidase buffers (PBS+0.03% $H_2O_2$). Following amplification, biosensors were washed in BB, incubated in 0.1 µg/ml streptavidin-peroxidase to load enzyme onto the biotin-BSA which has been adsorbed onto biosensors, and then bound enzyme was detected by biolayer interferometry in reactions using diaminobenzidine (DAB) as substrate (Vector Labs) in standard peroxidase buffer. Although bound enzyme may also be detected using BSA (200 µg/ml) added to chemiluminescent reagent, the DAB reaction gives faster rates and higher signals.

Amplification was assessed quantitatively for signal versus background, using reactions containing 50 attomoles of targets, a value near the lower limit of detection when not using nanoparticles. Backgrounds were measured in reactions without targets plus/minus amplification. Signal amplification was determined from reactions containing targets plus/minus amplification. The minus amplification reaction were biosensors held in BB while the plus amplification biosensors were reacted, since peroxidase loses activity when placed in $H_2O_2$ due to free radical attack on the enzyme. With conditions established that maximize amplification, target concentrations were varied to measure detection sensitivities (signal: noise $\geq 2$ at $p<0.05$).

LNA oligonucleotide capture probes (5' amino) were chemically crosslinked to aminopropylsilane biosensors (ForteBio) using Bioconjugate Toolkit reagents from Pierce (ThermoFisher). Yields were 0.1-0.2 pmole oligonucleotide per biosensor. LNA capture probes contained a 15 base 5' polydT spacer before the 7-9 base capture probe sequence. Examples of nucleic acid targets were 40 base oligonucleotides synthesized from conventional nucleotides (Midland) based upon the genomic sequence surrounding mutant sites in human mitochondrial DNA (termed $MELAS_{3243}$ and $MERRF_{8344}$). Capture probe/target pairs interrogating either the $MELAS_{3243}$ or $MERRF_{8344}$ mutations were used. Target oligonucleotides contained the mutant base within 15 bases of the 3' end, so that once annealed to LNA capture probes the overhanging 5' region of the target was available for hybridization to 3' biotinylated target detection oligonucleotides.

Coupling of Capture Probes to Biosensors:

Amine-reactive biosensors (ForteBio) were hydrated in PBS (phosphate buffered saline) and washed in 0.1M MES pH 5.0 (2-(N-morpholino ethanesulfonic acid)). Biosensors were activated by treatment for 10 mins in a solution composed of 0.1 M MES pH 5.0, 40 mg/ml EDC (1-ethyl-3-[3-dimethylaminopropyl]carbodiimide hydrochloride), 6 mg/ml NHS (N-hydrosulfosuccinimide). After activation, biosensors were immediately transferred to 30 ul solutions containing oligonucleotides (1 ug/ml; 5' or 3' amino terminated.) or antibody (35 ug/ml) in 0.1M MES pH 5.0. Biosensors were incubated for 12 hours, then washed with 0.1M MES pH 5.0 and stored at 4 C.

Biotinylated Colloidal Casein Substrate:

5% w/v casein colloid (Fitzgerald) is dialysed overnight against PBS. One ml of dialysed colloidal casein was reacted for 2 hours with EZ-Link LC-Biotin (4 mg dissolved in 50 ul DMSO; Pierce) at room temperature and the reaction products are dialysed for 24 hours against PBS. Biotinylated substrate is stored at 4 C.

Reaction Conditions for Binding of Streptavidin-Peroxidase to Biosensors:

Biosensors were incubated for variable periods of time in a solution composed of: 20 mM Tric-HCl, pH 7.5, 1 mM EDTA, 500 mM NaCl, 100 ug/ml BSA (bovine serum albumin), 100 ug/ml salmon sperm DNA, 0.1% Tween-20, 0.25% Pluronic F-127, 0.1% (w/v) casein colloid and 1 ug/ml streptavidin-horseradish peroxidase (Sigma, ultrasensitive).

Reaction Conditions for Peroxidase-Dependent Deposition of Biotinylated Colloidal Casein onto Biosensors:

Biosensors were incubated for variable periods of time at room temperature in a solution composed of 20 mM Tris-HCl, pH 7.5, 10 uM desferoxamine, 500 mM NaCl, 100 ug/ml BSA, 100 ug/ml salmon sperm DNA, 0.1% Tween-20, 50 uM dithiothreitol, 10 uM umbelliferone, 0.1% biotinylated colloidal casein.

Reaction Conditions for the Capture of DNA and RNA onto Biosensors:

Biosensors were incubated for variable periods of time in a 20 ul solution composed of 20 mM Tris-HCL, pH 7.5, 1 mM EDTA, 500 mM NaCl, 100 ug/ml BSA, 100 ug/ml salmon sperm DNA, 0.1% Tween-20 and either DNA or RNA targets at variable concentrations.

Reaction Conditions for the Capture of Proteins onto Biosensors:

Biosensors were incubated for variable periods of time in a 20 ul solution composed of 20 mM Tris-HCL, pH 7.5, 1 mM EDTA, 500 mM NaCl, 100 ug/ml BSA, 100 ug/ml salmon sperm DNA, 0.1% Tween-20, 0.5% casein colloid, and the protein target at variable concentrations.

Reaction Conditions for Tagging Captured DNA and RNA Targets with a Biotinylated Probe:

Probes were oligonucleotides terminated with biotin as sourced from commercial vendors. Oligonucleotides may also be labeled internally with biotins. Captured DNA or RNA targets were tagged with the biotinylated probe by incubation of biosensors for 30 mins in 20 ul of 20 mM Tris-HCL, pH 7.5, 1 mM EDTA, 500 mM NaCl, 100 ug/ml BSA, 100 ug/ml salmon sperm DNA, 0.1% Tween-20 plus the biotinylated oligonucleotide at variable concentrations.

Reaction Conditions for Tagging Captured Protein Targets with a Biotinylated Probe:

Probes may be antibodies that are biotinylated. They may be obtained commercially or unlabeled antibodies may be chemically biotinylated using EZ-Link biotin according to instructions provided by the manufacturer (Pierce). Protein targets which have been captured onto biosensors were tagged with biotin by incubation for 60 minutes in 20 ul of a solution composed of 20 mM Tris-HCL, pH 7.5, 1 mM EDTA, 500 mM NaCl, 100 ug/ml BSA, 100 ug/ml salmon sperm DNA, 0.1% Tween-20, 0.25% Pluronic F-127, 0.5% casein colloid plus 1 ug/ml of the biotinylated antibody probe.

Detection of Peroxidase Activity on Biosensors by Biolayer Interferometry:

Method 1: Biosensors were incubated for 10 mins. in Immobilon chemiluminescent HRP substrate (Millipore) containing 200 ug/ml BSA or 200 ug/ml non-fat dried milk. Method 2: Biosensors were incubated for 10 mins in ImmPACT DAB according to the manufacturer's instructions (Vector Labs).

Cycle Parameters for PxCR:

All operations were performed at room temperature. In the Examples described below the following method steps were included:

Step 1: 2 minute incubation of biosensors in a solution containing streptavidin-peroxidase (described above).

Step 2: 30 second incubation of biosensors in a wash solution composed of 2 M Guanidine hydrochloride, 1% (w/v) sarkosyl dissolved in 15 mM Tris-HCl, pH 7.5, 0.7 mM EDTA, 350 mM NaCl, 70 ug/ml BSA (bovine serum albumin), 70 ug/ml salmon sperm DNA, 0.07% Tween-20

Step 3. 2 minute incubation in solution of biotinylated colloidal casein substrate (described above).

Step 4. 30 second incubation in a wash solution composed of 20 mM Tris-HCl, pH 7.5, 1 mM EDTA, 500 mM NaCl, 100 ug/ml BSA (bovine serum albumin), 100 ug/ml salmon sperm DNA, 0.1% Tween-20, 0.25% Pluronic F-127, 0.1% (w/v) casein colloid Step 5: Back to Step 1 for a variable number of cycles Step 6: Incubation of biosensors in a solution for the detection of peroxidase activity (described above).

Parameters for Single Cycle PxCR:

Step 1: 30 minute incubation in a solution containing streptavidin-peroxidase (described above)

Step 2: 60 minute incubation in a solution containing biotinylated colloidal casein (described above).

Step 3: 10 minute incubation in a solution for detection of peroxidase activity as described above.

PxCR was implemented with the ForteBio OCTET. Biosensors were robotically controlled and can be incubated sequentially in any order through 12 different solutions. Incubations are performed in disposable 96-well plates at room temperature. Up to 8 separate biosensors were operated at one time for simultaneous analyses of different samples. Up to 96 biosensors in batches of 8 can be processed at one time so that samples can be repeatedly analyzed for 12 different targets. At the end of the run the sample can be recovered for storage and/or alternate analyses. The computer controlled ForteBio OCTET, has a desktop footprint of less than 4 ft$^2$.

Example 1

Figure 5:
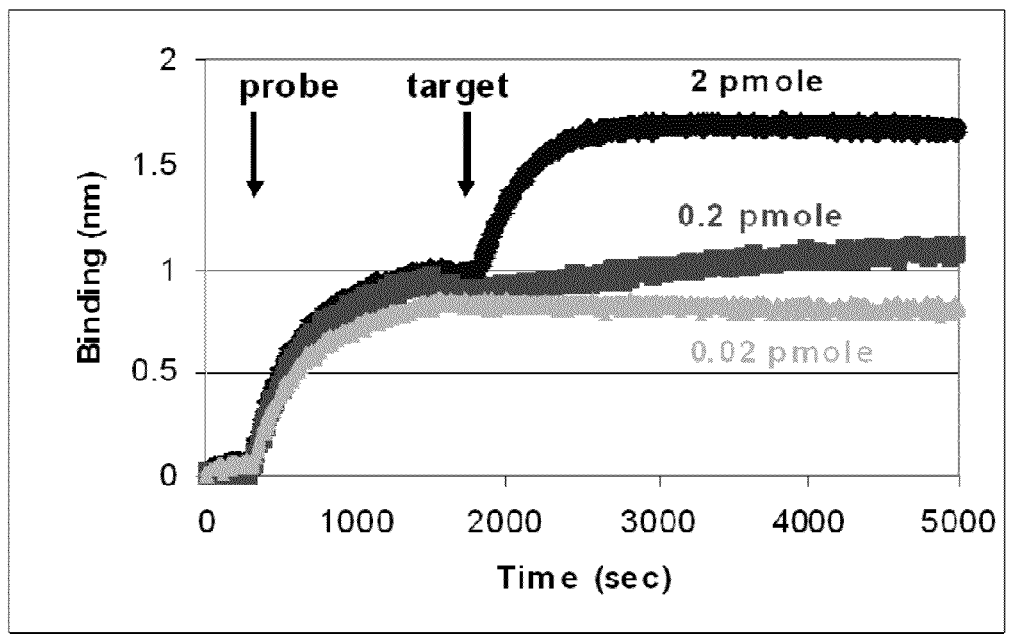
FIG. 5 illustrates real-time detection of DNA targets by conventional biolayer interferometry. Arrows indicate sequential transfer of streptavidin bound biosensors into 200 μl solutions (20 mM Tris-HCl pH 7.6, 1 mM EDTA, 500 mM NaCl, 0.1% Polysorbate 20 (TWEEN 20), 100 μg/ml BSA) containing biotinylated capture probe (10 pmoles), followed by transfer to a solution containing the target molecules (amounts as indicated). Binding capacity of streptavidin biosensors are ~1 pmole. Capture probe: 5' biotin-dT15 gcTCt-gcca (Locked nucleic acid (LNA) nucleotides in caps; targets: 5'-ccacccaagaaacagggtttgtaagatggcagagcccggt-3'(SEQ ID NO: 1).

Biotinylated capture probes were allowed to bind to streptavidin-coated biosensors. Binding of the capture probes to the immobilized streptavidin was rapid and saturable. Biosensors were then robotically moved into a solution containing the complementary target DNA. Binding (i.e., hybridization) of the target DNA to the capture probe/biosensor was also rapid and saturable. As expected from the 1:1 stoichiometry of DNA duplexes, the maximum signal from hybridization (0.75 nm shift) was nearly equal to the original signal from capture probe binding (0.85 nm shift). FIG. 5 shows that biolayer interferometry detected target DNA hybridizing in real-time to oligonucleotide capture probes immobilized onto the tip of the biosensor.

Example 2

Figure 6:
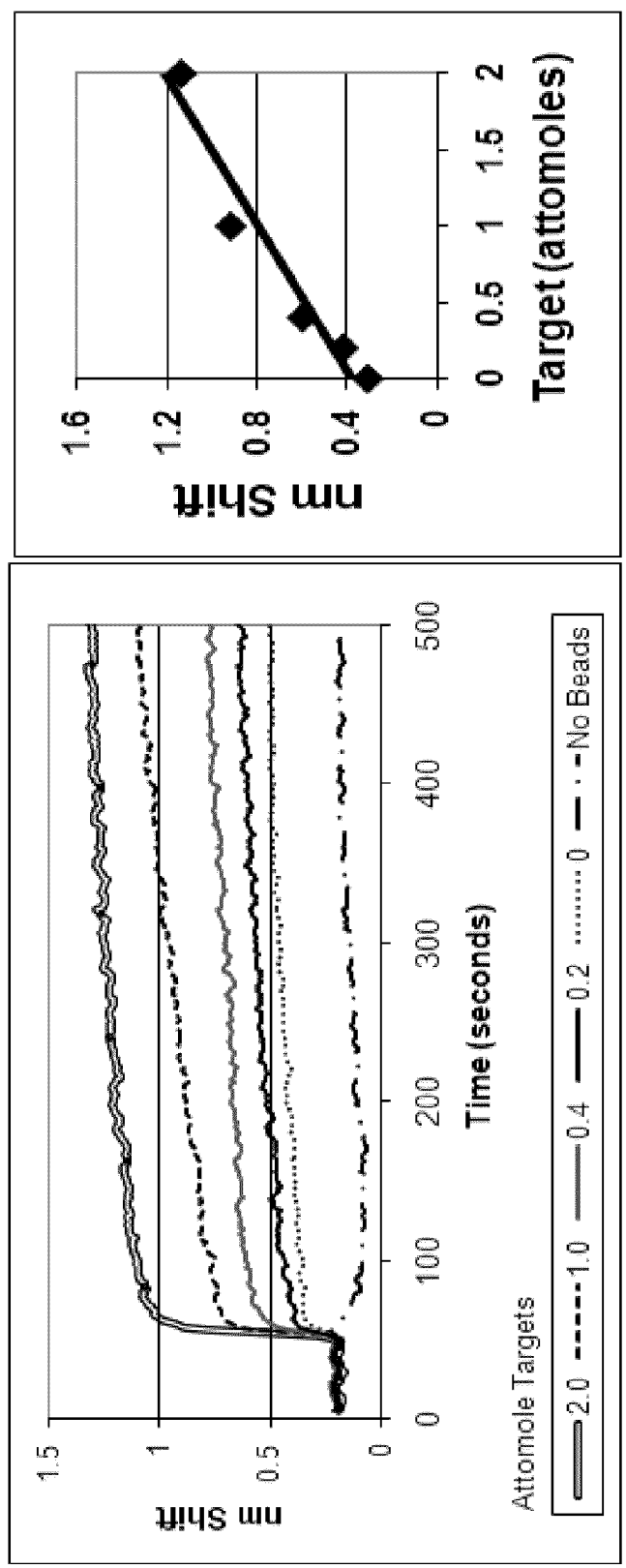
FIG. 6 illustrates the use of nanoparticles for the detection of targets (amounts as indicated) in 20 μl which hybridized to capture probes on biosensors, and were sequentially processed through solutions containing nanoparticles and peroxidase (see FIG. 3). Bound targets were detected in reactions containing hydrogen peroxide and protein (left). The majority of background signal is due to non-specific binding of nanoparticles as shown by the no bead (no target) control. Signals from 500 second time points are plotted versus amount of DNA target (right).

Although real-time detection of specific DNA targets is useful for many applications, the sensitivity of detection is limited to ~0.2 pmole DNA targets. To increase sensitivity the detection strategy was reconfigured so that bound DNA targets recruited multiple horseradish peroxidase enzymes (FIG. 3). Unlabeled targets bound indirectly to the biosensor by hybridization to the immobilized capture probe. They were then annealed to a target detection oligonucleotide that was biotinylated at a position that was available for binding. Incubation with streptavidin-conjugated-horseradish peroxidase then recruited peroxidase enzyme onto the biosensor tip. Horseradish peroxidase catalyses the degradation of hydrogen peroxide generating free radicals which can be donated to a variety of different acceptors, including proteins (Ostdal et al., (1999) Archives of Biochemistry & Biophysics 362:105-112, the contents of which are herein incorporated by reference in their entirety). Reacted proteins bind to the biosensor which is reported by biolayer interferometry. Ultrahigh detection sensitivity was accomplished by recruiting a "bag" of peroxidase molecules to each bound target using peroxidase-coated nanoparticles for signal amplification (FIG. 3). This amplification allowed detection of 0.2 attomole of DNA targets—i.e., 100,000 molecules (FIG. 6, left and right).

Example 3

Biotin-BSA Amplification

A biotinylated-protein may be used as a substrate to further amplify the signal from biosensor bound peroxidase enzymes (for an example of an intended application see FIG. 4). To provide proof of concept for the use of a biotinylated protein as a substrate for peroxidase recruited to the tip of a biosensor, a simplified experiment was designed. Peroxidase was bound to a biosensor by way of a biotin-streptavidin bridge. Specifically, streptavidin bound biosensors were incubated in 10 pg/ml biotin-peroxidase. The biosensor bound peroxidase was then allowed to react in a solution containing biotin-BSA so that the enzymatic activity would drive adsorption of biotin-BSA onto the biosensor. After washing in solution containing 100 ng/ml biotin, real-time biolayer interferometry was initiated. The control (Ct) and amplified (Amp Px) biosensors were incubated for 5 minutes in chemiluminescent reagent containing 10 μg/ml biotin-BSA+200 μg/ml normal BSA while the non-amplified biosensor (Px) was held in buffer only. Biotin at 100 ng/ml was also present during this incubation to ensure no binding of biotin-BSA to streptavidin biosensors due to biotin-streptavidin interactions. A subsequent incubation with streptavidin-peroxidase amplified the numbers of peroxidase enzyme bound to the biosensors. After further washing and incubation in streptavidin-peroxidase, bound enzyme was detected in reactions containing diaminobenzidine as substrate. As demonstrated in FIG. 7, signal amplification was 20-fold (0.8 nm shift Px versus 16 nm shift, Amp Px; amplification background control (Ct)<0.1 nm shift).

Example 4

Discrimination Technology

Figure 8:
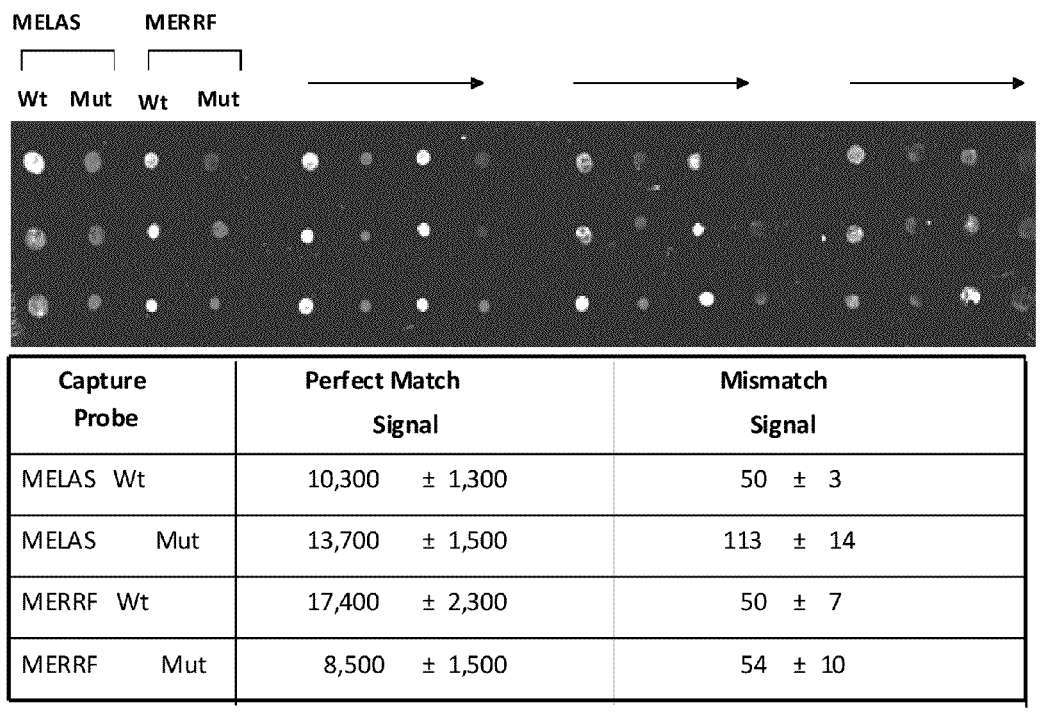
FIG. 8 illustrates the discrimination between wild-type and mutant targets representing human mitochondrial DNA sequences (MELAS and MERRF) using LNA capture probes and fluorescent detection on printed slides. Fluorescence due to bound targets was quantified by laser scanning and is expressed in arbitrary units.
Figure 9:
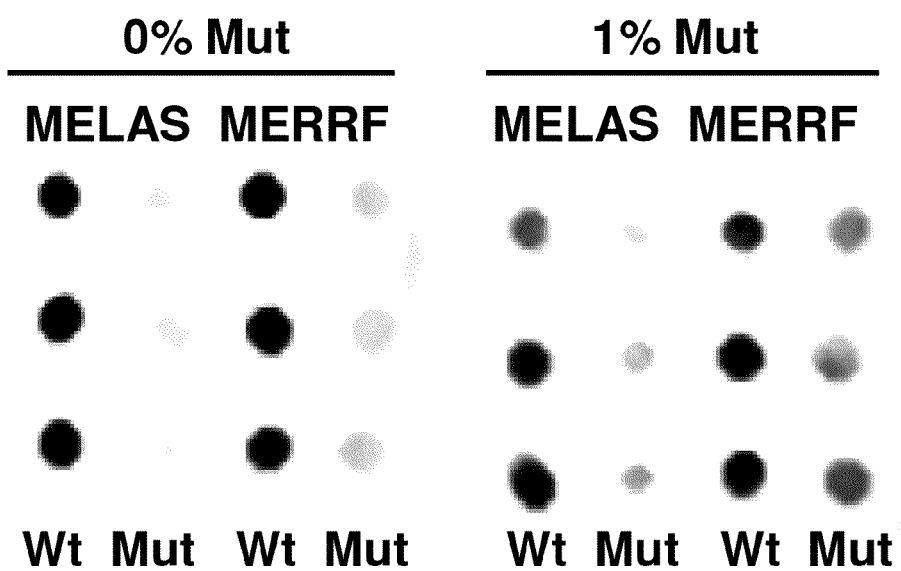
FIG. 9 illustrates the detection of mitochondrial DNA mutations at 1% frequency using 9-mer LNA oligonucleotides.
Figure 10:
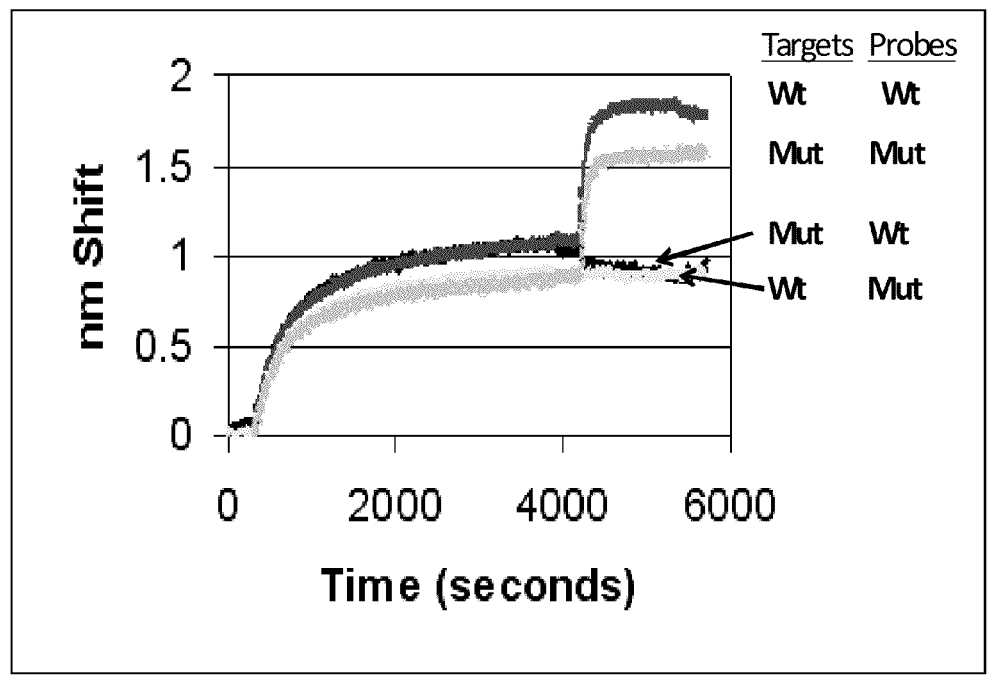
FIG. 10 illustrates the discrimination between wild-type and mutant targets by real-time biolayer interferometry. Capture probes: 5' biotinylated MELAS wild-type or mutant LNA oligonucleotides as indicated; targets: unlabeled conventional oligonucleotides having either the wild-type or mutant genomic sequence at the MELAS site as indicated in the legend on the right. Streptavidin biosensors were first incubated for 1 hour in 20 nM capture probe solutions and then after a brief wash moved into 20 nM target solutions.

Detection of mitochondrial DNA mutations requires not only high sensitivity but also high discrimination. This is because mutant molecules are often mixed with an excess of wild-type molecules. An example of high discrimination using 9-mer LNA oligonucleotides is shown in FIG. 8 where hybridizations were performed on glass slides. Here, LNA capture probes were designed that detected two commonly found mutations in mitochondrial DNA, termed MELAS$_{3243}$ and MERRF$_{8344}$. Both of those mutations are A→G substitutions and capture probes were designed to specifically detect either mutant or wild-type sequences. LNA capture probes (5' amino) were printed onto glass aldehyde slides and then hybridized to fluorescently labeled target DNAs synthesized from conventional nucleotides. For both MELAS and MERRF sequences, the wild-type targets were labeled with AlexaFluor555 (green) while the mutant targets were labeled with AlexaFluor647 (red). All four targets (1 nM each) were mixed together and hybridized to the array. As can be seen in FIG. 8, the specificity of those LNA capture probes was very high so that discrimination between mutant and wild-type targets was equally high. Such high discrimination allows LNA capture probes to detect mutations at 1% frequencies. Mixtures of mutant and wild-type targets were generated where the amount of the mutant was 1% relative to the wild-type (0.01 nM versus 1 nM, respectively). For these examples, targets were end-labeled with biotin and visualization of bound targets on the array was performed using horseradish peroxidase conjugated to streptavidin and chemiluminescent detection. In comparison to the no mutant control, both MELAS and MERRF mutants were readily detected at a 1% level (FIG. 9). This same discrimination occurs when LNA capture probe oligonucleotides are attached to biosensors (FIG. 10).

Example 5

Streptavidin-Peroxidase (SA-Px) is recruited onto biosensors by binding to the biotinylated tagging probe as illustrated in FIG. 11A. DNA oligonucleotide targets in the indicated amounts were annealed to biosensors in 20 ul of binding buffer (B: 20 mM Tris pH 7.5, 500 mM NaCl, 1 mM EDTA, 0.1% Tween-20, 100 ug/ml BSA) for 12 hours at room temperature. All subsequent steps were performed robotically in 96-well plates. SA-Px (1 ug/ml) was bound to biosensors in BB+0.5% colloidal casein for 15 min. After further processing and washes, bound peroxidase (Px) activity was measured with a diaminobenzidine-based substrate (ImmPact DAB: Vector Labs). Shown are the enzymatic reaction traces for all 8 biosensors. (FIG. 11B, Left Panel): From those traces the signal was quantified based upon initial enzymatic rates (FIG. 11B, Right Panel).

Example 6

Figure 12:
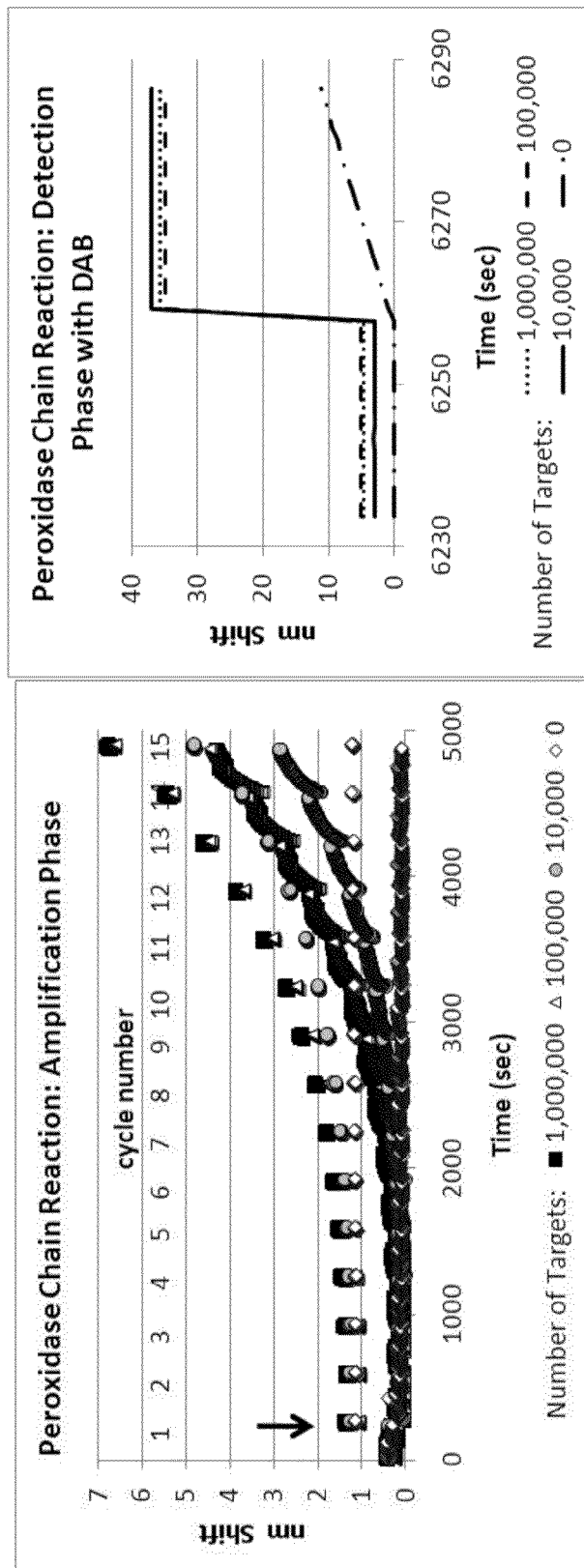
FIG. 12 illustrates real-Time PxCR for DNA Targets. A cycle consists of SA-Px—GuHCL/sarkosyl wash-biotinylated substrate—buffer wash. The arrow points to the first guanidine wash step. Biosensors were incubated with the indicated amount of DNA oligonucleotide targets in 20 ul BB for 1 hour before starting PxCR (left panel). At the end of cycle 15 of the amplification phase, biosensors were washed and then moved at time 6260 sec into DAB solutions for detection of Px activity (right panel).

PxCR improves sensitivities into the range of ≧one hundred molecules by introducing a form of signal amplification into the method illustrated in FIG. 2. The Inventor discovered that biotinylated casein (colloidal casein, Fitzgerald Industries,) is a substrate for peroxidase in the absence of added hydrogen peroxide. Peroxidase activity without added hydrogen peroxide has been described, as has the ability of some proteins to serve as substrates for the enzyme. By cycling biosensors between solutions containing biotinylated casein and SA-Px, the amounts of those proteins are amplified exponentially on the biosensor In this example using DNA targets, amplification is reported in real-time as signals from biosensors are recorded while they robotically move back and forth between amplifying and intervening wash solutions. Amplification is most clearly appreciated from the signal traces of biosensors that were immersed for 30 seconds in a 2M GuHCl/1% sarkosyl wash solution, as indicated by the arrow (FIG. 12, left panel). At the end of the amplification phase, bound Px can be detected based on its enzymatic activity by incubation of biosensors in DAB (FIG. 12, right panel). In this example, the amount of Px bound to target biosensors was too high for the time resolution of the instrument (1.6 sec/data point) to distinguish among the biosensors based upon initial enzymatic rates. The vastly increased sensitivity for detecting bound Px by its enzymatic activity, however, is shown by the significant background rate detected with the negative control biosensor, a background not evident from the traces of that biosensor (FIG. 12, left panel).

Example 7

Figure 13:
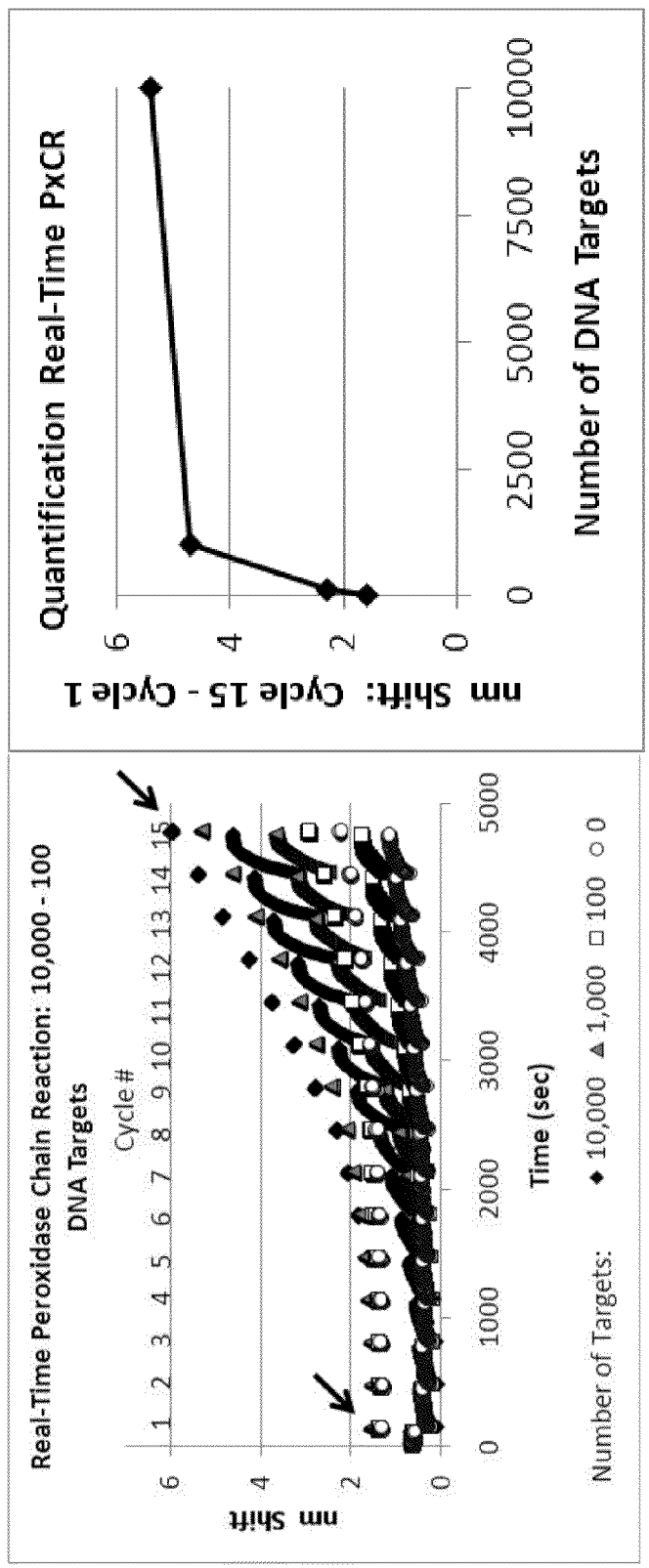
FIG. 13 illustrates real-time PxCR detection of as few as 100 DNA Targets. Biosensors were incubated overnight in 20 ul of BB containing the indicated number of DNA oligonucleotide targets ("0" target samples contain the biotinylated tagging probe but with a non-homologous target) (left panel). Signal quantification was based on the Δ nm shifts recorded in the guanidine wash steps (cycle 15-cycle 1; arrows). Cycle times: SA-Px and Biotin-colloid: 2 mins; wash steps: 30 secs (right panel).

Signal amplification allows PxCR to detect targets with ultrasensitivity. FIG. 13 left panel, shows that real-time PxCR was able to detect as few as 100 DNA targets. Quantification of the signal at the end of cycle 15 suggests that signal detection may become saturated above 1,000 targets under these conditions (FIG. 13, right panel).

Example 8

Figure 14:
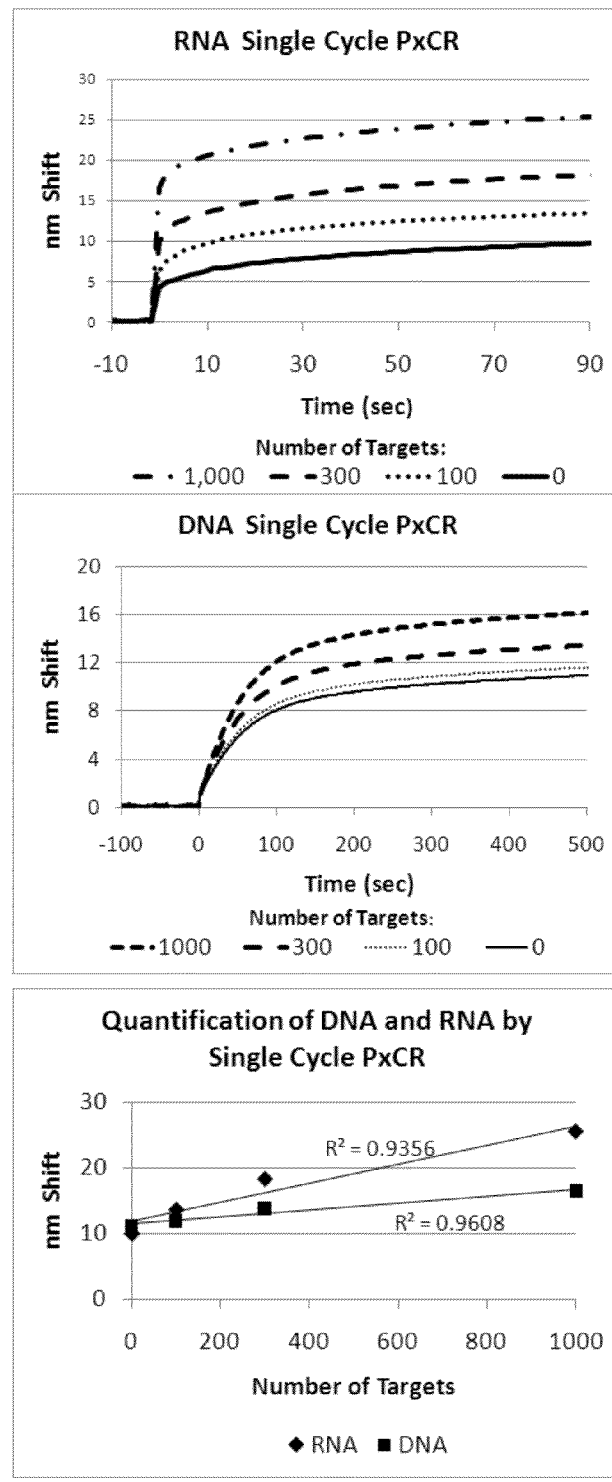
FIG. 14 illustrates single cycle PxCR for the detection of RNA, and DNA: Biosensors were incubated with the indicated amounts of oligonucleotide DNA or RNA targets (both with the same nucleotide sequence; amounts based upon OD260 measurements of stock solutions) for 20 hours in 20 ul BB. After binding SA-Px, biosensors were incubated for 1 hr in biotinylated colloidal casein (0.1% w/v). Shown are enzymatic activity traces with DAB substrate either in Immobilon (Millipore; top panel) or ImmPact (Vector Labs; middle panel). Quantification (bottom panel) was based on Δ nm shifts at plateau.

It was demonstrated that the deposition of biotinylated casein onto biosensors persisted for up to 2 hours when low amounts of SA-Px are bound (data not shown). Thus, single cycle amplifications can be performed by prolonged incubation of biosensors in biotinylated casein to build up the level of deposited substrate. At the end of the amplification phase, subsequent incubation of biosensors in SA-Px followed by incubation in DAB reported the number of targets based on the enzymatic activity of the amplified, bound SA-Px. In single cycle format, PxCR detected as few as 100 DNA and RNA targets (FIG. 14).

Example 9

Figure 15:
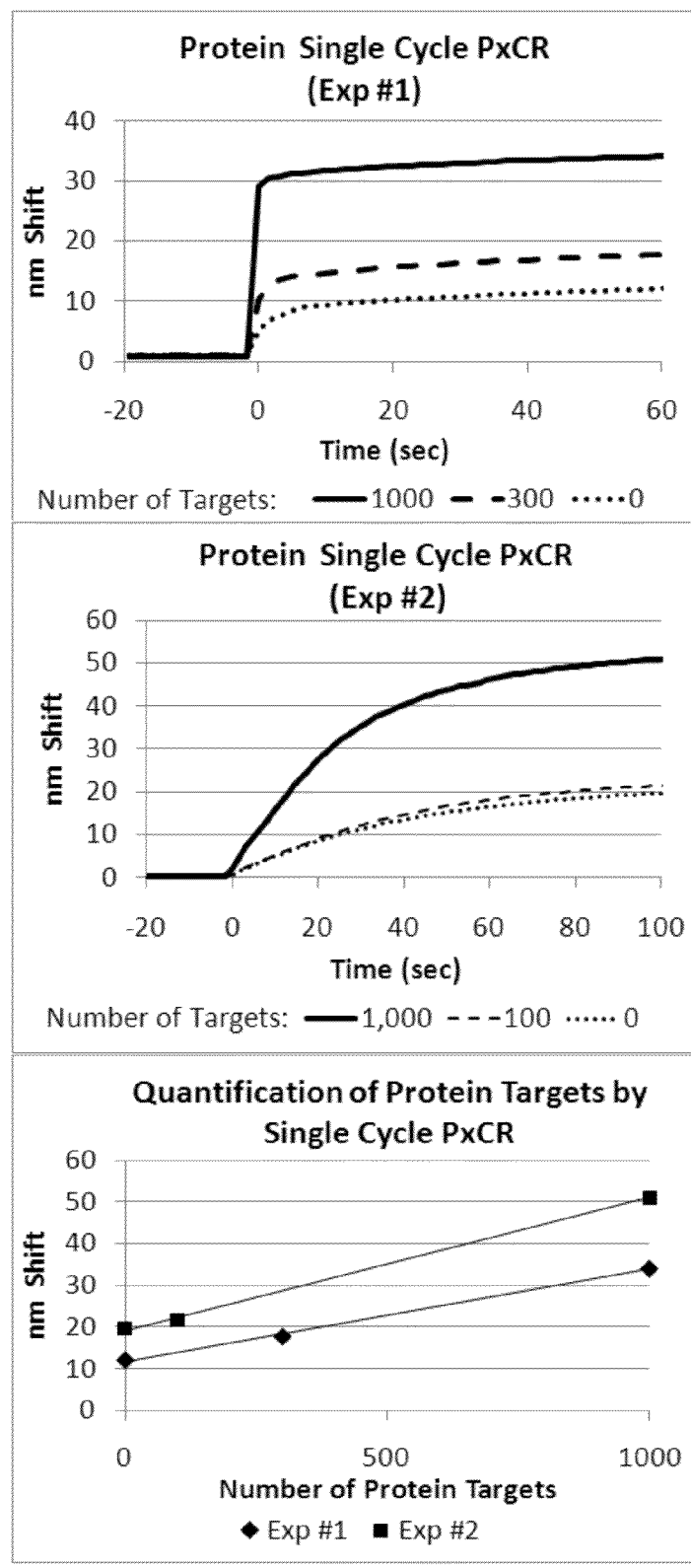
FIG. 15 illustrates single cycle PxCR for the detection of proteins: Biosensors were tethered with anti-avidin antibody (Vector Labs) and incubated with the indicated amount of avidin tetramers (Vector Labs; 1 ug/ml stock solutions) for 24 hours in BB. Following capture, bound avidin was tagged by incubation for 1 hour with the same antibody but in a biotinylated version (Vector Labs; all solutions contained high amounts of free biotin). After binding SA-Px, biosensors were incubated for 1 hr in biotinylated colloidal casein (0.1% w/v). Shown are enzymatic activity traces with DAB substrate either in Immobilon (Millipore; top panel) or ImmPact (Vector Labs; middle panel). Quantification (bottom panel) was based on Δ nm shifts at plateau.

Single cycle PxCR is also capable of detecting as few as 100 protein molecules (FIG. 15). Biosensors were tethered with anti-avidin antibody (Vector Labs) and incubated with the indicated amount of avidin tetramers (Vector Labs; 1 ug/ml stock solutions) for 24 hours in binding buffer (BB). Following capture, bound avidin was tagged by incubation for 1 hour with the same antibody but in a biotinylated version (Vector Labs; all solutions contained high amounts of free biotin). After binding SA-Px, biosensors were incubated for 1 hr in biotinylated colloidal casein (0.1% w/v). Shown are enzymatic activity traces with DAB substrate either in Immobilon (Millipore; top panel) or ImmPact (Vector Labs; middle panel). Quantification (bottom panel) was based on Δ nm shifts at plateau. The Inventors was able to show that single cycle PxCR is also capable of detecting as few as 100 protein molecules.

All publications and patents cited in this specification are hereby incorporated by reference in their entirety. The discussion of the references herein is intended merely to summarize the assertions made by the authors and no admission is made that any reference constitutes prior art. Applicants reserve the right to challenge the accuracy and pertinence of the cited references.

What is claimed is:

1. A method of determining the amount of a target molecule based on the amount of peroxidase reaction product deposited on a biosensor, the method comprising:
   a) exposing the biosensor to a sample containing the target molecule, the surface of the biosensor comprising a capture probe with specific affinity for the target molecule,
   b) allowing the target molecule to bind to the capture probe,
   c) allowing a target detection molecule to bind to the target molecule,
   d) allowing a peroxidase enzyme to bind to the target detection molecule,
   e) allowing the peroxidase enzyme to react with colloidal casein in the presence of dithiothreitol and in the absence of $H_2O_2$ wherein a peroxidase reaction product is deposited on the biosensor,
   f) determining the amount of the peroxidase reaction product deposited on the biosensor using biolayer interferometry, and
   g) determining the amount of the target molecule based on the amount of the peroxidase reaction product deposited on the biosensor.

2. The method of claim 1, wherein the target molecule consists of a first oligonucleotide and the capture probe consists of a second oligonucleotide and the target detection molecule consists of a third oligonucleotide.

3. The method of claim 1, wherein the target molecule consists of a protein and the capture probe consists of an antibody.

4. The method of claim 1, wherein the target molecule consists of an oligosaccharide and the capture probe consists of a lectin.

5. The method of claim 1, wherein the peroxidase enzyme is bound to the target detection molecule using a bridging system.

6. The method of claim 1, wherein the peroxidase enzyme is bound to the target detection molecule by using a biotinylated target detection molecule and streptavidin-peroxidase.

7. The method of claim 1, wherein the target molecule consists of a protein and the capture probe consists of a first antibody and the target detection molecule consists of a second antibody.

8. The method of claim 1, wherein the target molecule consists of an oligosaccharide and the capture probe consists of a first lectin and the target detection molecule consists of a second lectin.

9. The method of claim 1, wherein the substrate is diaminobenzidine.

10. A method of determining the amount of a target molecule based on the amount of peroxidase reaction product deposited on a biosensor, the method comprising:
    a) exposing a biosensor to a sample containing the target molecule, wherein a surface of the biosensor comprises a capture probe with specific affinity for the target molecule,
    b) allowing the target molecule to bind to the capture probe,
    c) allowing a target detection molecule to bind to the target molecule,
    d) allowing a peroxidase enzyme to bind to the target detection molecule,
    e) allowing the peroxidase enzyme to react with biotinylated colloidal casein in the presence of dithiothreitol and in the absence of $H_2O_2$, wherein biotin is deposited on the biosensor,
    f) allowing streptavidin-peroxidase to bind to the biotin deposited on the biosensor,
    g) optionally repeating steps e) and f) as desired,
    h) allowing the peroxidase enzyme to react with a substrate, wherein peroxidase reaction products are deposited on the biosensor,
    i) determining the amount of the peroxidase reaction product deposited on the biosensor using biolayer interferometry, and
    j) determining the amount of the target molecule based on the amount of the peroxidase reaction products deposited on the biosensor.

11. The method of claim 10, wherein the target molecule consists of a first oligonucleotide and the capture probe consists of a second oligonucleotide and the target detection molecule consists of a third oligonucleotide.

12. The method of claim 10, wherein the target molecule consists of a protein and the capture probe consists of a first antibody and the target detection molecule consist of a second antibody.

13. The method of claim 10, wherein the target molecule consists of an oligosaccharide and the capture probe consists of a first lectin and the target detection molecule consists of a second lectin.

14. The method of claim 10, wherein the substrate is diaminobenzidine.

* * * * *

SEQUENCE LISTING

```
<160> NUMBER OF SEQ ID NOS: 1

<210> SEQ ID NO 1
<211> LENGTH: 40
<212> TYPE: DNA
<213> ORGANISM: Homo sapiens

<400> SEQUENCE: 1
ccacccaaga aacagggttt gtaagatggc agagcccggt                              40
```